United States Patent [19]

Garrett

[11] Patent Number: 5,765,555

[45] Date of Patent: Jun. 16, 1998

[54] APPARATUS FOR TREATING PATIENTS WITH OXYGEN

[75] Inventor: Michael E. Garrett, Woking, England

[73] Assignee: The BOC Group plc, Windlesham, England

[21] Appl. No.: 876,779

[22] Filed: Jun. 16, 1997

Related U.S. Application Data

[63] Continuation of Ser. No. 559,322, Nov. 16, 1995, abandoned.

[30] Foreign Application Priority Data

Dec. 13, 1994 [GB] United Kingdom ................... 9425072

[51] Int. Cl.$^6$ ........................................ A62B 31/00
[52] U.S. Cl. .................... 128/205.26; 128/202.12; 128/205.25
[58] Field of Search ................ 128/205.26, 200.13, 128/202.13, 202.16, 204.18, 205.25, 202.12, 200.24; 600/21, 22

[56] References Cited

U.S. PATENT DOCUMENTS 5,327,904  7/1994  Hannum .

FOREIGN PATENT DOCUMENTS

| A-2 660 548 | 11/1991 | France . | |
|---|---|---|---|
| C-86 540 | 11/1895 | Germany . | |
| A-18 08 201 | 5/1970 | Germany . | |
| 194646 | 2/1965 | Sweden | 128/205.26 |
| 537683 | 1/1977 | U.S.S.R. | 128/205.26 |
| 1600768 | 11/1988 | U.S.S.R. | 128/205.26 |
| 1600767 | 10/1990 | U.S.S.R. | 128/205.26 |
| 26953 | of 1902 | United Kingdom | 128/205.26 |

OTHER PUBLICATIONS

Japan Abstract—vol. 017 No. 037 (C–1019) 25 Jan. 1993.

Japan Abstract—JP-A-04 253860 (Matsushita Electric Ind. Co. Ltd.) 9 Sep. 1992.

*Primary Examiner*—Aaron J. Lewis
*Assistant Examiner*—William J. Deane, Jr.
*Attorney, Agent, or Firm*—R. Hain Swope; Salvatore P. Pace

[57] ABSTRACT

An apparatus for the ectopic treatment of a patient with oxygen comprises a circuit including a bath for receiving the patient, a container spaced from the bath and containing oxygenated liquid and a pump for circulating the oxygenated liquid between the container and the bath. Preferably, the bath is located in a hyperbaric chamber.

5 Claims, 1 Drawing Sheet

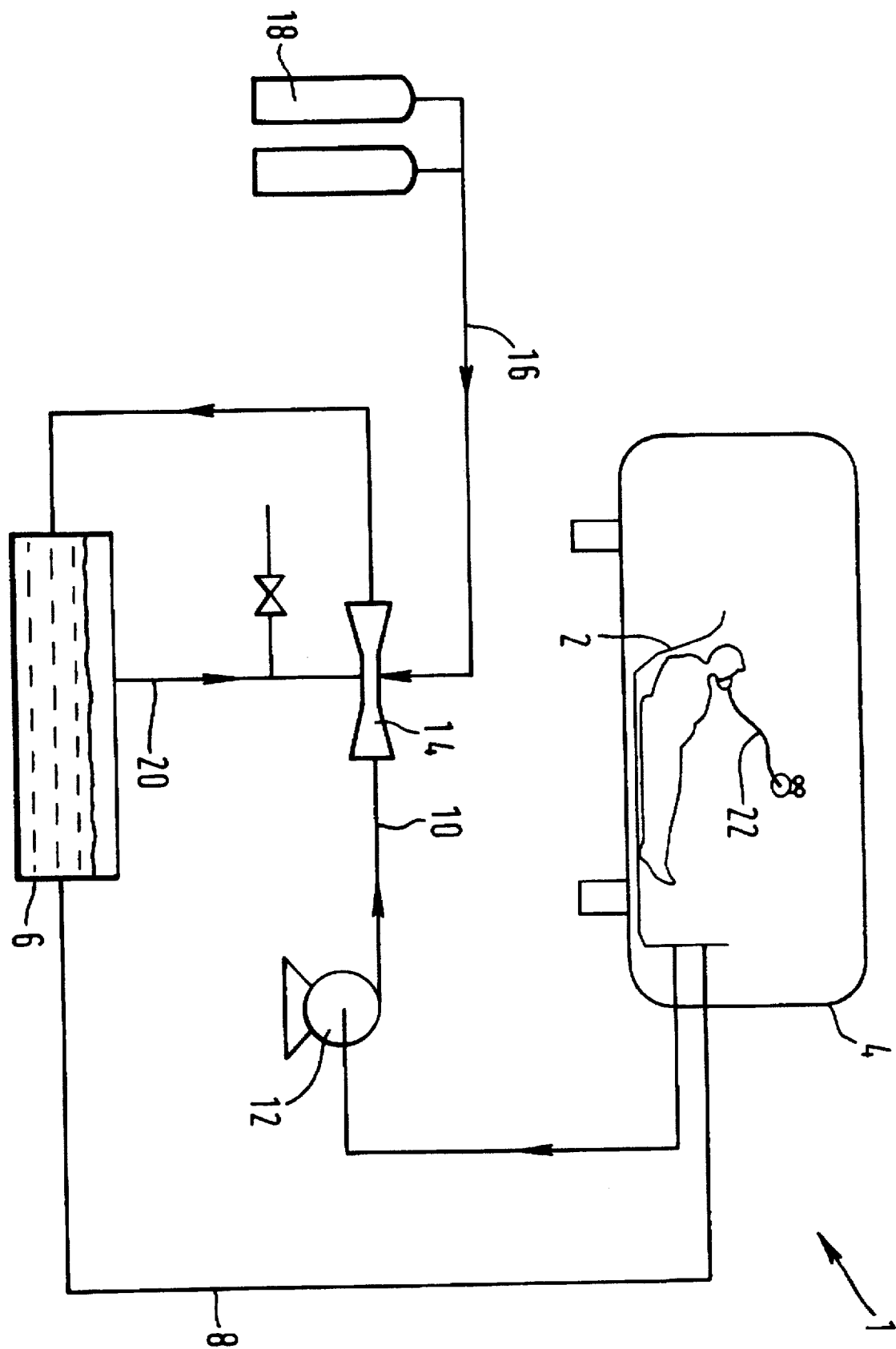

APPARATUS FOR TREATING PATIENTS WITH OXYGEN

This is a continuation of application Ser. No. 08/559,322 filed Nov. 16, 1995 of Michael E. Garrett for APPARATUS FOR TREATING PATIENTS WITH OXYGEN, now abandoned.

The present invention relates to apparatus for the ectopic treatment of patients with oxygen.

BACKGROUND OF THE INVENTION

It is known to place a patient in a chamber containing oxygen at high pressures to undergo radio therapy and various treatments of certain afflictions such as, for example, certain forms of poisoning, bacterial infections and poor healing wounds. Hyperbaric Oxygen up to 2 barapressure is often administered to patients by enclosing them in a pressure chamber which is pressurized with air. Breathing oxygen is provided to the patient through a mask. Such treatment has been shown to be effective in a number of illnesses, but its healing effect is limited to those tissues in direct contact with the oxygen. Furthermore, although the partial pressure of oxygen in the pressurized air surrounding the patient is increased relative to atmospheric, it is still relatively low.

In accordance with the present invention, there is provided an apparatus which will enable a patient to experience oxygen enhancement of up to 1 bar g partial pressure in the breathing gas while at the same time his or her cutaneous tissues can be exposed to oxygen partial pressures of 5 bar g. It is believed that this is particularly effective when bacterial infections of the skin are involved.

SUMMARY OF THE INVENTION

According to the present invention, an apparatus for the ectopic treatment of a patient with oxygen comprises a bath for receiving the patient, a source of oxygenated liquid spaced from the bath at which oxygen is dissolved and remains dissolved in the liquid and means for delivering the oxygenated liquid to the bath.

BRIEF DESCRIPTION OF THE DRAWING

The FIGURE is a diagrammatic drawing of an apparatus for the ectopic treatment of patients with oxygen.

DETAILED DESCRIPTION OF THE PREFERRED EMBODIMENT

The present invention provides an apparatus whereby a patient can be treated with oxygen via a bath having oxygen dissolved therein. The bath is preferably water, although other aqueous fluids may be utilized, depending on the requirements of the clinical situation. While a patients may be treated with about 2 bar g of oxygen in a bath in accordance with the present invention, it is preferred that the bath be contained in a hyperbaric chamber as the oxygen treatment may be increased therein to about 5 bar g.

An embodiment of the invention will now be described by way of example, reference being made to the FIGURE, wherein an apparatus 1 for exposing the skin of a patient to contact with an oxygenated liquid, such as water, is illustrated in diagrammatic drawing. The apparatus 1 includes a bath 2 for the patient positioned within a hyperbaric chamber 4. In the FIGURE, the bath 2 is located in a circuit which includes a source of oxygenated water including a container 6 spaced from the bath 2, a first pipeline 8 from the container 6 to the bath 2 and a second pipeline 10 from the bath 2 to the container 6 in which is located both a pump 12 and a venturi 14.

A third pipeline 16 extends from a source 18 of gaseous oxygen under pressure towards the venturi 14 and a fourth pipeline 20 extends from the upper (as illustrated) surface of the container 6 again towards the venturi 14.

In use, a patient is placed in the bath 2 and is supported by water saturated with oxygen. The water, which may be at body temperature, is gently circulated through the circuit by the pump 12. The water leaving the bath 2 through the pipeline 10 passes through the venturi 14 where it is re-oxygenated by the passage of fresh oxygen from the source 18 passing through the pipeline 16. Any excess oxygen in the ullage space above the water level in the container 6 passes through the pipeline 20 towards the venturi 14 where it adds to the re-oxygenation of the water. The oxygen dissolved in the water contained within container 6 will remain dissolved during its delivery to and whilst it remains in the bath 2.

In this embodiment, where the bath 2 is positioned in the hyperbaric chamber 4, the chamber 4 can be pressurized by means known per se to approximately 5 bar a and the patient can wear a breathing mask which will include a tube 22 for the passage therethrough of a breathable gas e.g. air, at a pressure of approximately 5 bar a. The pressure of the breathing gas is adjusted to compensate for the pressure in the chamber 4.

The gas breathed by the patient through line 22 can be a mixture such as oxygen/helium which avoids the increased density of the pressurized gas and is far easier to breathe. Replacing nitrogen with helium has the additional advantage of reducing the risk of nitrogen dissolving in the blood during the prolonged periods of treatment that may be required in certain clinical situations.

The atmosphere above the bath and within the hyperbaric chamber can be air or air enriched with nitrogen at a pressure approximately equal to that of the oxygen in the bath. this pressure prevents significant quantities of oxygen from escaping the bath. It is, however, contemplated to monitor the atmosphere by conventional means, not shown, for oxygen enrichment and replacing it with air or nitrogen-enriched air at the same pressure should it be necessary to do so. This is a distinct advantage of the present invention in that the patient can be externally exposed to higher partial pressures of oxygen in an apparatus which avoids any risk of fire inherent in the presence of oxygen-enriched gas.

I claim:

1. An apparatus for the ectopic treatment of a patient with oxygen comprising a bath located in a hyperbaric chamber for receiving a patient, a source of oxygenated liquid spaced from the bath at which oxygen is dissolved in the liquid to a pressure of from about 2 to about 5 bar, means for pressurizing the chamber to a pressure equal to that of the oxygen in the liquid, so that the oxygen remains dissolved in the liquid, means for delivering the oxygenated liquid to the bath, said chamber further including a tube for the passage therethrough of a breathable gas for use by a patient when in the bath, the pressure in said tube being approximately that in said chamber.

2. An apparatus in accordance with claim 1, wherein the delivery means includes a pump for circulating the oxygenated liquid between said source and the bath.

3. An apparatus in accordance with claim 1, wherein the source of oxygenated liquid includes a container for the oxygenated liquid to which is connected a source of gaseous oxygen under pressure.

4. An apparatus in accordance with claim 3, wherein a venturi is located between the source of gaseous oxygen and the container for oxygenated liquid.

5. An apparatus in accordance with claim 1, wherein the oxygenated liquid is oxygenated water.

* * * * *